(12) United States Patent
Liddell (10) Patent No.: US 9,447,171 B2
(45) Date of Patent: Sep. 20, 2016

(54) PURIFICATION PROCESS FOR FRAGMENT ANTIBODIES

(75) Inventor: John Macdonald Liddell, Cleveland (GB)

(73) Assignee: Fujifilm Diosynth Biotechnologies UK Limited, Billingham (GB)

( * ) Notice: Subject to any disclaimer, the term of this patent is extended or adjusted under 35 U.S.C. 154(b) by 359 days.

(21) Appl. No.: 13/122,676

(22) PCT Filed: Oct. 2, 2009

(86) PCT No.: PCT/GB2009/002363
§ 371 (c)(1),
(2), (4) Date: Apr. 11, 2011

(87) PCT Pub. No.: WO2010/040988
PCT Pub. Date: Apr. 15, 2010

(65) Prior Publication Data
US 2011/0190478 A1 Aug. 4, 2011

(30) Foreign Application Priority Data
Oct. 6, 2008 (GB) .................................. 0818228.9

(51) Int. Cl.
| C07K 1/14 | (2006.01) |
| C07K 1/36 | (2006.01) |
| C07K 1/30 | (2006.01) |
| C07K 16/06 | (2006.01) |
| C07K 16/24 | (2006.01) |
| C07K 19/00 | (2006.01) |
| C07K 16/00 | (2006.01) |
| C07K 16/40 | (2006.01) |

(52) U.S. Cl.
CPC .............. *C07K 16/065* (2013.01); *C07K 1/14* (2013.01); *C07K 1/36* (2013.01); *C07K 16/00* (2013.01); *C07K 16/241* (2013.01); *C07K 16/40* (2013.01); *C07K 2317/55* (2013.01); *C07K 2317/569* (2013.01)

(58) Field of Classification Search
None
See application file for complete search history.

(56) References Cited

U.S. PATENT DOCUMENTS

| 5,196,323 A | 3/1993 | Bodo et al. |
| 2005/0080009 A1* | 4/2005 | Metzner ................. A61K 38/39 530/382 |
| 2006/0269977 A1* | 11/2006 | Sawadaishi et al. ........ 435/7.92 |
| 2007/0292442 A1* | 12/2007 | Wan ......................... C07K 1/18 424/176.1 |

FOREIGN PATENT DOCUMENTS

| EP | 1561756 A1 * | 8/2005 |
| WO | 2004/092393 | 10/2004 |
| WO | 2008/079280 | 7/2008 |
| WO | 2008/091740 | 7/2008 |

OTHER PUBLICATIONS

Denton et al. "Direct isolation of monoclonal antibodies from tissue culture supernatant using the cation-exchange cellulose express-ion S" J. Chromatography A, 908 (2001), 223-234.*
Brigido et al. "Role of mouse VH10 and VL gene segments in the specific binding of antibody to Z-DNA analyzed with recombinant single chain Fv molecules" J. Immunology, 150(2), 469-479, 1993.*
Lecerf et al. "Autoreactivity of human VH domains from cDNA libraries: Analysis with a bacterial expression system" J. Immunology, 161, 1274-1283, 1998.*
Persson et al. "Purificaiton of antibody and antibody-fragment from E. coli homogenate using 6.9-Diamino-2-ethoxyacridine lactate as precipitation agent", Biotechnology and Bioengineering, 87(3), 2004.*
Lydersen, Acid Precipitation of Mammalian Cell Fermentation Broth, Annals New York Academy of Sciences, 745, 222-231, 1994.
Hardy, Large-Scale Production of Recombinant Hepatitis B Surface Antigen from Pichia Pastoris, Journal of Biotechnology, 77, 157-167, 2000.
Ljunglof, Ion Exchange Chromatography of Antibody Fragments, Biotechnology and Bioengineering, 96, 515-524, 2007.

* cited by examiner

*Primary Examiner* — Daniel E Kolker
*Assistant Examiner* — James Rogers
(74) *Attorney, Agent, or Firm* — Morgan, Lewis & Bockius LLP (57) ABSTRACT

A process for purification of a fragment antibody from a culture medium also comprising at least one impurity is provided. The purification is carried out after the pH of the culture medium has been reduced to a pH at which the fragment antibody is soluble, but one or more of the impurities are insoluble. A process for the preparation of a fragment antibody employing such a purification process is also provided.

20 Claims, 7 Drawing Sheets

Figure 1

| Lane | Sample |
|---|---|
| 1 | MWM |
| 2 | anti-TNF α Load |
| 3 | anti-TNF α pellet pH 6 |
| 4 | anti-TNF α S/N pH 6 |
| 5 | anti-TNF α pellet pH 5 |
| 6 | anti-TNF α S/N pH 5 |
| 7 | anti-TNF α pellet pH 4 |
| 8 | anti-TNF α S/N pH 4 |

Figure 2

| Lane | Sample |
|------|--------|
| 1 | Molecular Weight Marker |
| 2 | Blank |
| 3 | Capto MMC pool |
| 4 | Blank |
| 5 | Capto S pool |
| 6 | Blank |
| 7 | SP-XL Sepharose pool |

Figure 3

D1.3 Fab

| Lane | Sample |
|---|---|
| 1 | D1.3 Load |
| 2 | D1.3 pellet pH 6 |
| 3 | D1.3 S/N pH 6 |
| 4 | D1.3 pellet pH 5 |
| 5 | D1.3 S/N pH 5 |
| 6 | D1.3 pellet pH 4 |
| 7 | D1.3 S/N pH 4 |

Figure 4

D1.3
Fab

| Well | Sample |
|---|---|
| 1 | MW marker |
| 2 | Blank |
| 3 | Elution fraction A8 |
| 4 | Elution fraction A9 |
| 5 | Elution fraction A10 |
| 6 | Elution fraction A11 |
| 7 | Elution fraction A12 |
| 8 | Elution fraction A13 |
| 9 | Elution fraction A14 |
| 10 | Elution fraction A15 |
| 11 | Elution fraction B1 |
| 12 | Elution fraction B2 |

Figure 5

| Lane | Sample | pH | Conductivity (mS/cm) |
|---|---|---|---|
| 1 | Mol wt marker | | |
| 2 | HEL4 | 7 | 5 |
| 3 | HEL4 | 7 | 15 |
| 4 | HEL4 | 7 | 30 |
| 5 | HEL4 | 6 | 5 |
| 6 | HEL4 | 6 | 15 |
| 7 | HEL4 | 6 | 30 |
| 8 | HEL4 | 5 | 5 |
| 9 | HEL4 | 5 | 15 |
| 10 | HEL4 | 5 | 30 |
| 11 | HEL4 | 4 | 5 |
| 12 | HEL4 | 4 | 15 |
| 13 | HEL4 | 4 | 30 |
| 14 | HEL4 | 3 | 5 |
| 15 | HEL4 | 3 | 15 |
| 16 | HEL4 | 3 | 30 |

Figure 6

| Lane | Sample | pH | Conductivity (mS/cm) |
|---|---|---|---|
| 1 | Mol wt marker | | |
| 2 | Tandab | 7 | 5 |
| 3 | Tandab | 7 | 15 |
| 4 | Tandab | 7 | 30 |
| 5 | Tandab | 3 | 5 |
| 6 | Tandab | 3 | 15 |
| 7 | Tandab | 3 | 30 |
| 8 | Blank | | |
| 9 | Blank | | |

Figure 7

| Lane | Sample | pH | Conductivity (mS/cm) |
|------|--------|----|----|
| 1 | Mol wt marker | | |
| 2 | D1.3 | 7 | 5 |
| 3 | D1.3 | 7 | 15 |
| 4 | D1.3 | 7 | 30 |
| 5 | D1.3 | 5 | 5 |
| 6 | D1.3 | 5 | 15 |
| 7 | D1.3 | 5 | 30 |
| 8 | D1.3 | 3 | 5 |
| 9 | D1.3 | 3 | 15 |
| 10 | D1.3 | 3 | 30 |
| 11 | Blank | | |
| 12 | Blank | | |

PURIFICATION PROCESS FOR FRAGMENT ANTIBODIES

The present invention concerns a process for the purification of fragment antibodies (fAbs).

Fragment antibodies (fAbs) are of increasing importance in a range of therapeutic areas. One of the most important methods of producing fAbs is by recombinant technology. Such techniques use a host cell to express the desired fAb, which is then separated from the production medium and purified. EP1561756 discloses the use of a range of pHs, including acidic pH, for the separation of proteins from nucleic acid contaminants. The culture medium is purified by affinity chromatography prior to the pH treatment, or the sample of protein employed is previously purified and spiked with contaminant DNA prior to the low pH treatment. WO2006/101441 discloses a process for purification of thermostable amelin and amelogenin proteins by treatment with acetic acid followed by heat treatment. WO96/33208 discloses a process for the purification of fAbs comprising chromatographic purification of the fAb isolated from the culture medium, followed by low pH hydrophobic interaction chromatography.

According to one aspect of the present invention, there is provided a process for purification of a fragment antibody from a culture medium also comprising at least one impurity, wherein the purification is carried out after the pH of the culture medium has been reduced to a pH at which the fragment antibody is soluble, but one or more of the impurities are insoluble.

According to a second aspect of the present invention, there is provided a process for the preparation of a fragment antibody comprising:

a) preparing a culture medium comprising a fragment antibody and at least one impurity;

b) purifying the fragment antibody from the culture medium, wherein the purification is carried out after the pH of the culture medium has been reduced to a pH at which the fragment antibody is soluble, but one or more of the impurities are insoluble.

According to a third aspect of the present invention, there is provided a process for the separation of an impurity from a culture medium comprising a fragment antibody and at least one impurity, which comprises reducing the pH of the culture medium to a pH at which the fragment antibody is soluble, but one or more of the impurities are insoluble, and separating the insoluble impurity from the culture medium.

Culture media employed in the present invention are those having a pH of greater than pH 6, preferably greater than 6.5. Whilst higher pH culture media may be employed in certain instances, typically the pH is no greater than 8. Most preferably the pH is from 6.7 to 7.5, especially about 7.

Fragment antibodies which can be purified by the process of the present invention are sections of antibodies comprising an immunoglobulin domain or an assembly of immunoglobulin domains and which are capable of binding to an antigen, and which, in many embodiments, comprise at least one heavy chain, commonly a $V_H$ chain, or a functional fragment thereof, or a light chain, commonly a $V_L$ chain, or a functional fragment thereof, together with at least one other chain. In certain embodiments, the fAb comprises a heavy chain and a light chain, each chain being made up of a constant domain and a variable domain, such as a Fab. In other embodiments, the fAb comprises two or more domains, typically a combination of either the variable and constant domains of either heavy or light chains, combinations of variable domain from two heavy chains, combinations of variable domains from two light chains, or a combination of the variable domain from a light chain and the variable domain from a heavy chain. In some embodiments, the fAb comprises the $V_H$ and $V_L$ domains joined by flexible polypeptide linker preventing dissociation (single chain Fv, scFv). In yet further embodiments, the fAb comprises a single domain, or a fragment thereof, typically either the variable heavy chain or a fragment thereof, or the variable light chain or a fragment thereof. In still further embodiments, the fAb is a multimeric format, such as a bis scFv, $Fab_2$, $Fab_3$, minibody, diabody, triabody, tetrabody or tandab.

Examples of fAbs that can be purified by the process of the present invention include protein or polypeptide constructs comprising a combined heavy chain and a light chain, each chain being made up of a constant domain and a variable domain where such immunoglobulin light and heavy chains interact to form a single functional antigen-binding site.

Further examples include $V_H$ chain-based domain antibodies, being polypeptides which are capable of binding to a target, the polypeptide comprising at least one binding domain, wherein the binding domain is a single variable domain of a variable heavy chain antibody or a functional fragment thereof.

Yet further examples include $V_L$ chain-based domain antibodies, being polypeptides which are capable of binding to a target, the polypeptide comprising at least one binding domain, wherein the binding domain is a single variable domain of a variable light chain antibody or a functional fragment thereof.

In many embodiments, the fAbs purified by the process of the present invention have a pI greater than 5, preferably greater then 5.5 and most preferably greater than 6.

Methods of purifying fAbs are well known in the art and include precipitation, crystallisation and chromatography. Combinations of such methods may be employed if desired. Chromatography is the most preferred method of purification.

Methods of chromatographic purification of fAbs are well known in the art. Examples of such methods include ion exchange chromatography, particularly cation-exchange chromatography; chromatography based on hydrophobicity, such as hydrophobic interaction chromatography (HIC), reverse phase chromatography, hydrophobic charge induction chromatography, and mixed mode chromatography; size-based purifications such as size exclusion chromatography and gel filtration; and affinity chromatography. One or more chromatography steps can be employed if desired, particularly two or more chromatography steps comprising two or more different methods, for example affinity chromatography followed by ion-exchange chromatography.

In certain embodiments, the chromatographic purification comprises affinity chromatography. Affinity chromatography methods and media which can be employed to purify a fAb are known in the art and are selected by virtue of having selective binding properties for the target fAb. Examples of such methods include Protein A affinity chromatography and Protein G affinity chromatography. In certain preferred embodiments, the affinity chromatography medium comprises a synthetic affinity ligand having the formula:

wherein

Q represents an attachment to a solid support matrix, optionally via a spacer group;

A and B are each independently Y-phenyl or Y-naphthyl groups substituted with one or more substituents capable of hydrogen bonding, preferably one or more of —OH, —SH or —CO$_2$H groups;

each Y independently represents —NR—, —O— or —S—; and each R independently represents H or a C$_{1-4}$ alkyl group.

Preferred affinity ligands are compounds of formula:

wherein Q represents an attachment to a solid support matrix, optionally via a spacer group, and A and B are each independently —NH-phenyl or —NH-naphthyl groups substituted with one or more of —OH, —SH or —CO$_2$H groups. When either of A or B represent phenyl, a substituent, most preferably —OH, is preferably located at the position meta or para to the bond to the —NH moiety. Especially preferred affinity ligands include compounds of formula:

wherein Q represents an attachment to a solid support matrix, optionally via a spacer group.

Spacer groups which can be represented by Q include optionally substituted aminoalkylamino moieties, such as a group of formula —NH—(CH$_2$)$_n$NH-G where n is a positive integer up to 12, preferably from 2-6 and G is a solid support matrix; —NH—(CH$_2$)$_n$O-G where n and G are as previously defined; -0-(CH$_2$)$_n$O-G where n and G are as previously defined; -0-(CH$_2$CH$_2$)$_n$O-G where n and G are as previously defined; —NH—(CH$_2$)$_n$O-G where n and G are as previously defined; —NH—(CH$_2$)$_n$NH—(CH$_2$)$_x$O-G where n and G are as previously defined, and x is from 1 to 6. One or more of the —CH$_2$-moieties my be substituted by one or more substituents, for example OH or NH$_2$ groups.

Solid support matrices to which the affinity ligands can be attached are well known in the field of affinity chromatography, and include synthetic polymers, such as polyacrylamide, polyvinylalcohol or polystyrene, especially cross linked synthetic polymers; inorganic supports, such as silica-based supports; and particularly polysaccharide supports, for example starch, cellulose or agarose.

In certain embodiments, excellent results have been achieved using the supported affinity ligands commercially available from Prometic Biosciences under the tradenames MAbsorbent A1P and MAbsorbent A2P.

Contact between the medium containing a fAb and the supported affinity ligands is effected under conditions where the fAb binds to the affinity ligand. In many embodiments, an aqueous solution comprising fAb at about neutral pH (for example a pH from about 6 to 8, for example 6.5 to 7.5, and especially a pH of 7. The aqueous solution preferably has a low ionic strength, such as an ionic strength of less than 50 mS/cm, for example between 10 and 40 mS/cm, and preferably 30 mS/cm. Contact is preferably continued until substantially all of the fAb is bound to the affinity ligand. Many impurities which may be present in the medium comprising the fAb do not bind to the affinity ligand and therefore remain in the medium.

Commonly, the supported affinity ligand is employed in a chromatography column, and the medium comprising the fAb is flowed through the column. A single pass through the column may be employed, or as alternatives, the medium can be recirculated through the column. Two or more columns may be employed in sequence.

The support comprising the bound fAb may be washed with one or more wash solutions under conditions where the fAb remains bound, for example employing aqueous buffers of low ionic strength, and about neutral pH.

The fAb can then be separated from the affinity ligand by contact with a solution which causes the fAb to be released from the ligand, for example by varying the ionic strength. In many embodiments, the elution solvent comprises an aqueous solution having a lower pH than the medium from which the fAb was attached to the ligand, for example an buffer solution having a pH in the range of from 2 to 4. If desired, an elution gradient can be employed.

In preferred embodiments, the chromatographic method comprises ion exchange chromatography, and especially cation exchange chromatography. Weak or strong cation exchange resins may be employed. Commonly, strong cation exchange resins comprise supported organic groups comprising sulphonic acid or sulphonate groups, depending upon the pH. Weak cation exchanger resins commonly comprise supported organic groups comprising carboxylic acid or carboxylate groups, depending upon the pH. In certain embodiments, multimodal cation exchange resins, which incorporate additional binding mechanisms as well as the ionic interactions, for example one or more of hydrogen bonding interactions and hydrophobic interactions. Examples of suitable cation exchange resins are well known in the art.

In the method of the present invention, the pH of the culture medium is preferably reduced to a pH less than 6.0, commonly less than 5.5, most preferably less than 5. In many embodiments, a pH of greater than 2.5, most commonly 3.0 or more, typically 3.5 or more and preferably greater than 4 is employed. In many preferred embodiments, the pH is reduced to a pH in the range of from 3 to 5, commonly from 4 to 5, such as from 4 to 4.5.

In embodiments where the fAb has a pI less than the pH of the culture medium, especially a pI of less than 5.5, the pH of the culture medium is advantageously reduced to a pH which is greater than 0.5 pH units different from the pI of the fAb, and preferably at least 1 pH unit different from the pI. Where the pI of the fAb is low, such as 3.0 or less, the pH is preferably reduced to a pH which is at least 0.5 pH units greater than the pI. Where the pI of the fAb is relatively high, such as from 5 to 5.5, the pH is preferably reduced to a pH which is at least 0.5 pH units less than the pI.

In certain preferred embodiments of the present invention, the reduction in pH is accompanied by a reduction in the ionic strength of the culture medium. Commonly, the ionic strength is reduced to a conductivity of 5 mScm$^{-1}$ or less.

In other preferred embodiments of the present invention, especially where the fAb has a pI close to the pH to which the culture medium is reduced, such as within 0.5 pH units of such pH, the ionic strength is not reduced, and may advantageously be increased. In such embodiments, an ionic strength of 20 mScm$^{-1}$ or more, such as 25 mScm$^{-1}$, for example from 27 to 50 mScm$^{-1}$ can advantageously be employed.

The pH of the culture medium can be reduced by addition of acid until the required pH is achieved. In many embodiments, the acid comprises a buffer solution. In certain especially preferred embodiments, the culture medium is contacted with a buffer having the desired pH by dialysis or diafiltration. The use of dialysis or diafiltration enables the concomitant reduction in pH and ionic strength of the culture medium.

The culture medium comprising the fAb is commonly obtained by expression of recombinant host cells encoding the fAb. The host cell may be prokaryotic or eukaryotic. Examples of prokaryotic cells include bacterial cells, for example gram-negative bacterial cells, including *E. coli, Salmonella typhimurium, Serratia marsescens* and *Pseudomonas aeruginosa*, and gram-positive bacterial cells including *Bacillus subtilis*. Examples of eukaryotic cells include yeasts, such as *Pichia pastoris, Saccharomyces cerevisiae, Hansenula polymorpha, Kluyveromyces lactis, Schizosaccharomyces pombe*. Mammalian host cells which can be employed include human cell lines, such as human embryonic kidney and PERC.6 cells; murine cell lines, such as NS0 cells; and particularly hamster cell lines such as baby hamster kidney cells and especially Chinese hamster ovary cells. Other eukaryotic host cells such as those of filamentous fungi, plant, insect, amphibian cells or ovarian species may also be employed. Preferred host cells are bacteria, particularly enterobacteriacae, preferably *E. coli*, and especially B or K12 strains thereof.

Host cells are cultured using methods known in the art for the cell concerned. It will be recognised that the fAb may be secreted from the host cell, or may be retained within the cell, or a combination of both. fAb retained within the host cell may be obtained by cell lysis or disruption using methods known in the art, such as physical disintegration, for example by high shear mixing or high pressure homogenisation, and chemical methods, such as treatment with an alkaline detergent, such as SDS.

In addition to the target protein, the culture medium commonly comprises impurities such as one or more of intact cells, partly disintegrated cells, cell wall components, cell fragments, nucleic acids and native host cell proteins.

Insoluble components in the culture medium may be removed by physical separation, for example filtration or centrifugation prior to reduction of pH to below 6. Subsequent to reduction of pH, insoluble components in the culture medium are preferably removed by physical means, most preferably filtration or centrifugation. Preferably, no physical separation to remove insoluble components occurs prior to the pH reduction step. When filtration is employed, either normal flow or tangential flow methods may be employed. Filter media useful in such methods are well known in the art. Subsequent to removal of removal of insoluble components after reduction of pH, the pH may be increased, for example to about neutral pH, such as from 6 to 8, preferably from 6.5 to 7.5, prior to subsequent purification of the fAb.

The present invention is illustrated without limitation by the following examples.

EXAMPLE 1

A domain antibody fragment (an anti TNF α domain) was produced by periplasmic expression in a recombinant *E. coli* strain. The fragment domain has a total molecular weight of 12 kDa and was secreted into the cell periplasm and subsequently into the fermentation growth medium. At the end of fermentation levels of anti TNF α fragment domain present were around 2.3 g/L Initial isolation of anti TNF α fragment domain involved centrifugation to remove cellular material with subsequent filtration through a 0.45/0.2 micron filter. The resulting clarified solution had a conductivity of 29 mS/cm and a pH of 6.8.

Three aliquots of this centrifuged and filtered supernate were dialysed against three different buffers for 16 hours.
1. 25 mM sodium acetate, pH 4.0
2. 25 mM sodium acetate, pH 5.0
3. 25 mM potassium phosphate, pH 6.0

Following dialysis each sample was centrifuged and the solids and supernatant collected separately. The conductivities of the dialysed solutions were in the range 2.5-4 mS/cm Reducing SDS PAGE gels were run of both solid and supernatant fraction for each sample against a sample of the untreated supernate giving the results shown in FIG. 1.

Figure 1:
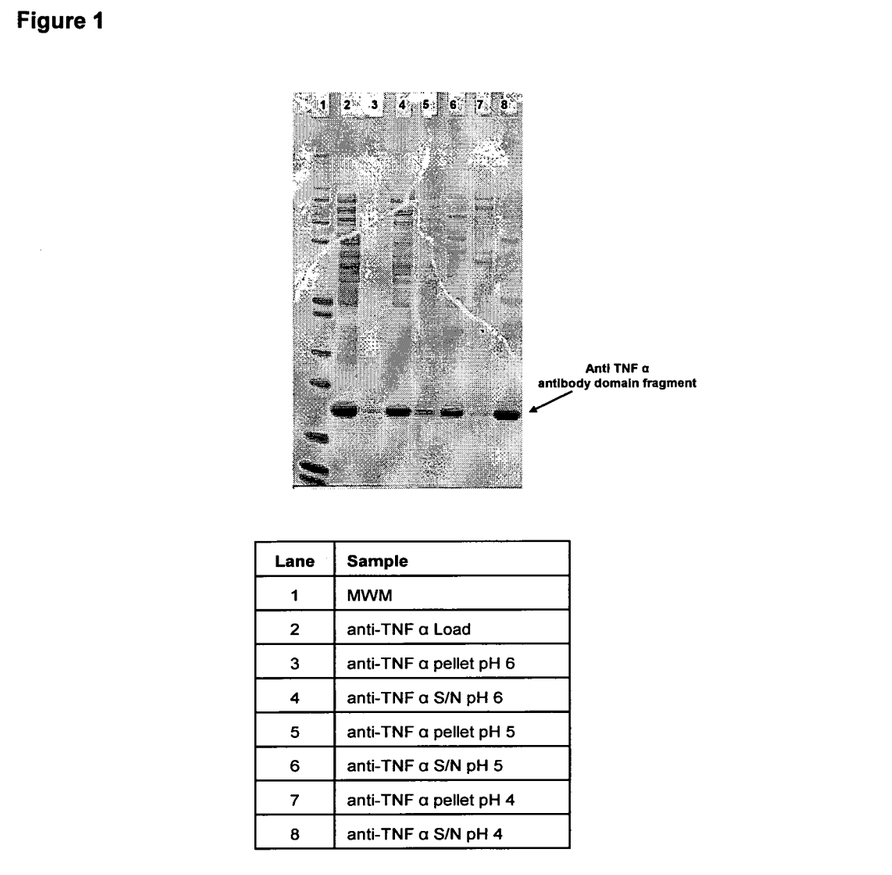
FIG. 1 shows SDS PAGE gel results for samples against a sample of the untreated supernate.

The effect of lowering the pH together with the change in buffer resulted in increasing amounts of host cell protein being removed while the domain fragment remained in solution at all conditions as seen by the negligible amounts of the domain fragment present in the solids (pellet) fraction. The trend for the highest purification from host cell impurities was pH4>pH 5>pH 6.

Material treated in this way by dialysis into 25 mM sodium acetate, pH 5, then centrifuged to remove precipitated solids, was purified using three different cation exchange media (Capto MMC, Capto S and SP XL Sepharose (all GE Healthcare). Columns of 10 cm bed height were used and purification of the domain fragment carried out using identical protocols. Material was loaded on to each column to ca 17 g domain fragment/ml of media. The columns were equilibrated with 25 mM sodium acetate, pH 5.0 and eluted with a linear gradient to 25 mM sodium acetate, 1M NaCl, pH 5.0 over 15 column volumes. The linear flow rate was 120 cm/hr.

Figure 2:
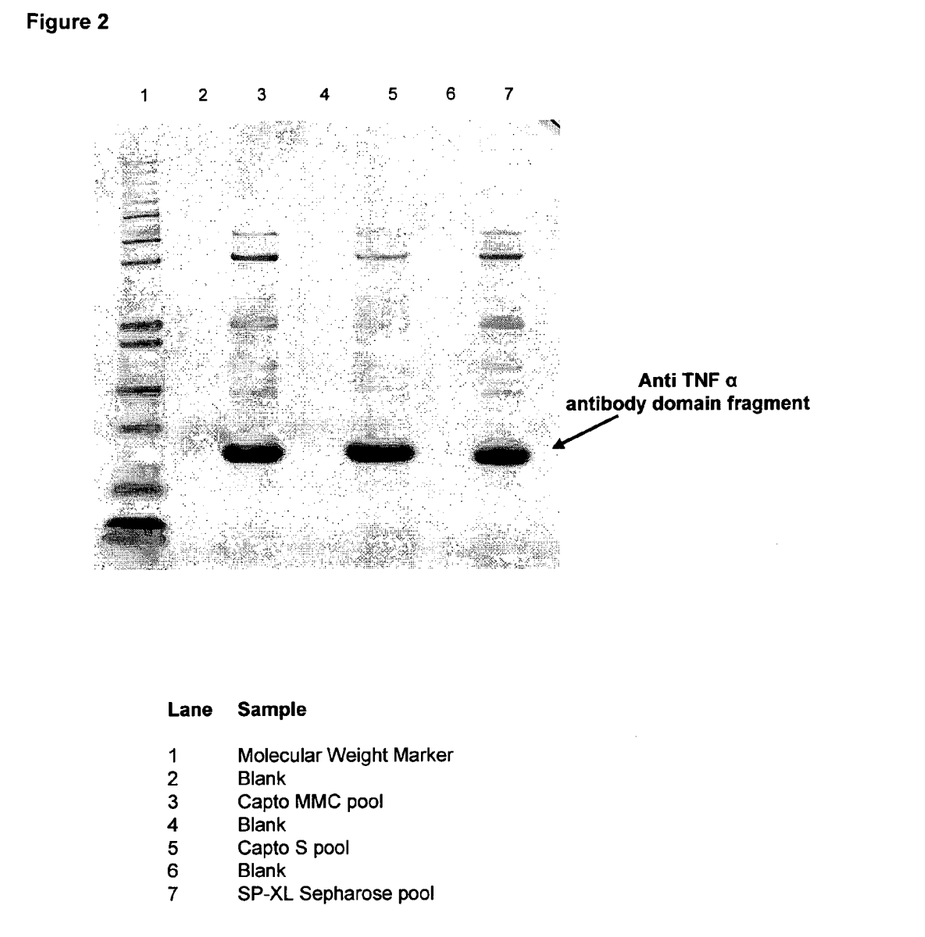
FIG. 2 shows additional SDS PAGE gel results for samples including highly purified fragment.

All runs produced domain fragment which was highly purified as seen by SDS PAGE analysis, the results of which are shown in FIG. 2.

EXAMPLE 2

An Fab (from the monoclonal anti lysozyme antibody D1.3) was produced by periplasmic expression in a recombinant E. coli strain. The Fab with a total molecular weight 47.4 kDa (comprising two chains—one chain made up of a variable light domain with constant domain attached and a second chain made up of a variable heavy domain with constant domain attached) was secreted into the cell periplasm and subsequently into the fermentation growth medium. At the end of fermentation levels of D1.3 present in the fermenter supernatant were around 100 mg/L.

Initial isolation of Fab D1.3 involved centrifugation to remove cellular material with subsequent filtration through a 0.45/0.2 micron filter. The resulting clarified solution had a conductivity of 29.3 mS/cm and a pH of 6.7.

Three aliquots of this centrifuged and filtered supernate were dialysed against three different buffers for 16 hours.
1. 25 mM sodium acetate, pH 4.0
2. 25 mM sodium acetate, pH 5.0
3. 25 mM potassium phosphate, pH 6.0

Following dialysis each sample was centrifuged and the solids and supernatant collected separately. The conductivities of the dialysed solutions were in the range 2.5-4 mS/cm Reducing SDS PAGE gels were run of both solid and supernatant fraction for each sample against a sample of the untreated supernate giving the results shown in FIG. 3.

Figure 3:
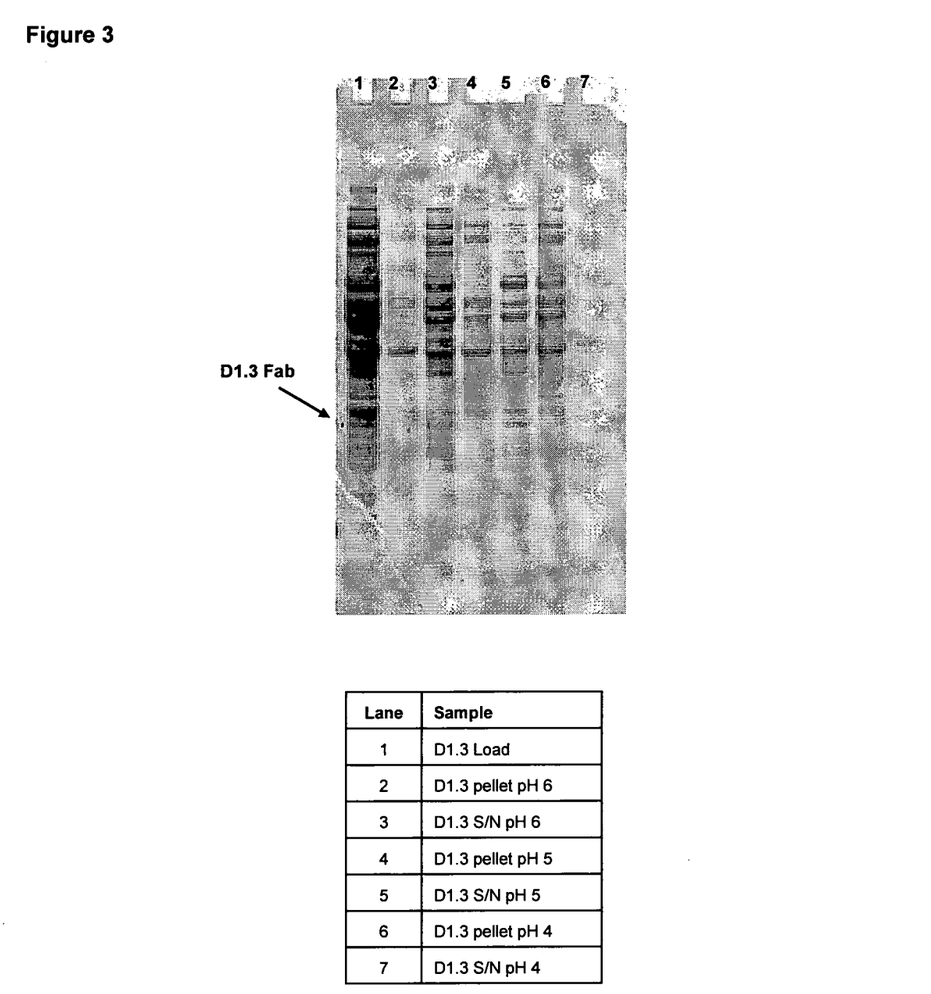
FIG. 3 shows additional SDS PAGE gel results for samples against a sample of the untreated supernate.

The effect of lowering the pH together with the change in buffer resulted in increasing amounts of host cell protein being removed while the domain fragment remained in solution at all conditions as seen by the negligible amounts of the Fab fragment present in the solids (pellet) fraction. The trend for the highest purification from host cell impurities was pH4>pH 5>pH 6.

Material treated in this way by dialysis into a 25 mM sodium acetate, pH 6, then centrifuged to remove precipitated solids, was purified using cation exchange media (SP Sepharose; GE Healthcare). A column of 2 cm bed height were used and purification of the Fab fragment. The column was equilibrated with 25 mM sodium acetate, pH 6.0 and eluted with a linear gradient to 25 mM sodium acetate, 1M NaCl, pH 6.0 over 10 column volumes. The linear flow rate was 120 cm/hr.

Figure 4:
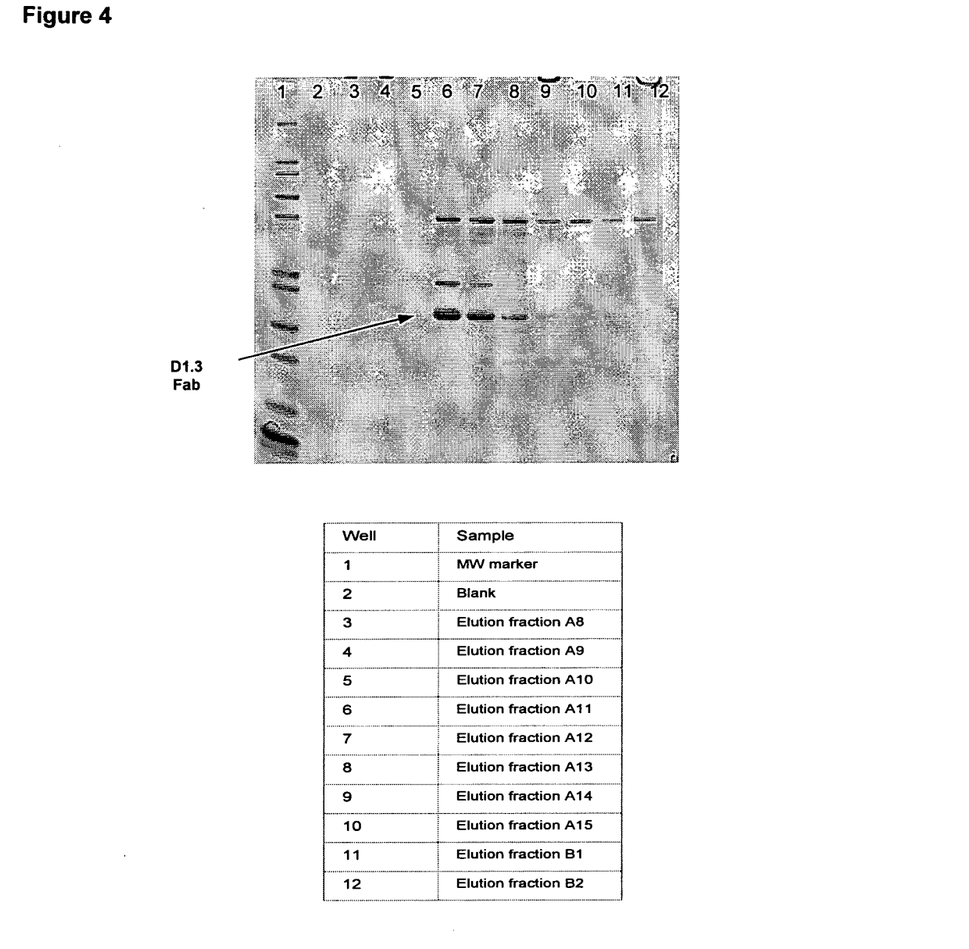
FIG. 4 shows additional SDS PAGE gel results for samples including highly purified Fab fragment.

All runs produced a Fab fragment which was highly purified as seen by SDS PAGE analysis, the results of which are shown in FIG. 4.

EXAMPLE 3

A $V_H$ based domain fragment (anti hen egg white lysozyme domain HEL4—Jespers et at J Mol Biol (2004) 337 893-903) was produced by periplasmic expression in a recombinant E. coli strain. The domain with a molecular weight 12.8 kDa was secreted into the cell periplasm and subsequently into the fermentation growth medium. At the end of fermentation levels of the HEL4 domain present in the fermenter supernatant was around 1.5 g/L.

Initial isolation of HEL4 involved centrifugation to remove cellular material with subsequent filtration through a 0.45/0.2 micron filter. The resulting clarified solution had a conductivity of ca 31 mS/cm and a pH of 6.9.

Three aliquots of this centrifuged and filtered supernate were dialysed into a matrix of different buffers for 16 hours.

| | Conductivity | | |
|---|---|---|---|
| pH | 5 mS/cm | 15 mS/cm | 30 mS/cm |
| 7 | 25 mM sodium phosphate | 25 mM sodium phosphate, 115 mM NaCl | 25 mM sodium phosphate, 275 mM NaCl |
| 6 | 25 mM sodium phosphate | 25 mM sodium phosphate, 115 mM NaCl | 25 mM sodium phosphate, 275 mM NaCl |
| 5 | 25 mM sodium acetate | 25 mM sodium acetate, 115 mM NaCl | 25 mM sodium acetate, 275 mM NaCl |
| 4 | 25 mM sodium acetate | 25 mM sodium acetate, 115 mM NaCl | 25 mM sodium acetate, 275 mM NaCl |
| 3 | 25 mM sodium citrate | 25 mM sodium citrate, 115 mM NaCl | 25 mM sodium citrate, 275 mM NaCl |

Following dialysis each sample was centrifuged and the solids and supernatant collected separately.

Figure 5:
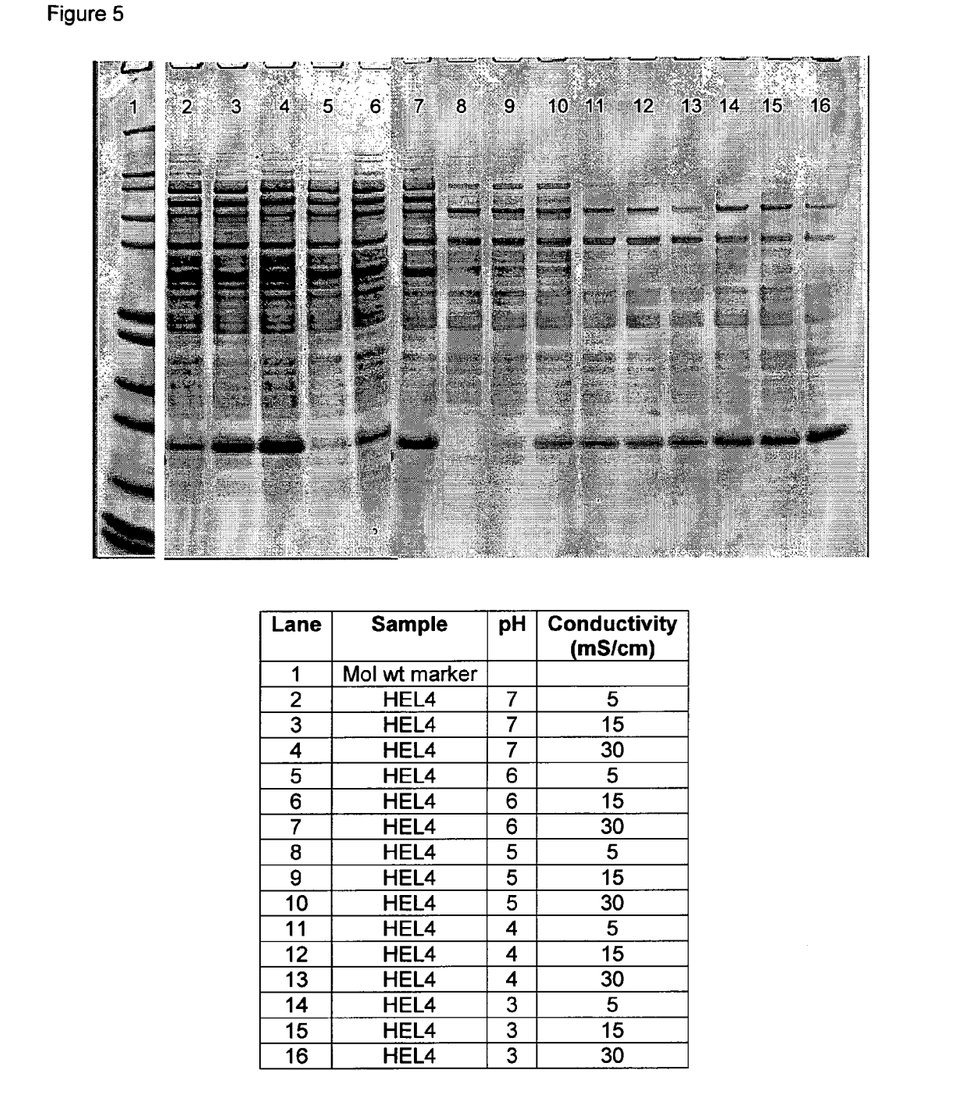
FIG. 5 shows additional SDS PAGE gel results for samples against a sample of the untreated supernate.

Reducing SDS PAGE gels were run of the supernatant fraction for each sample against a sample of the untreated supernate giving the results shown in FIG. 5.

The effect of lowering the pH results in a reduction in host cell proteins which is mainly independent of conductivity over the range studied. The HEL4 antibody fragment is maintained in solution at lower solution pH providing a purification of the antibody fragment relative to the host cell proteins. The data shows that under some conditions (pH 5) much of the HEL4 antibody fragment is not retained in solution and is precipitated with the host cell proteins. This arises due to the pI of the protein (ca 4.8). At lower pH the antibody fragment remains in solution while the host cell proteins are precipitated.

EXAMPLE 4

A multivalent antibody fragment derived tandem antibody fragment (tandab composed of two chains each containing four domains (two $V_H$ and two $V_L$ domains in the format $(V_H V_L V_H V_L)_2$ as described in Example 15 of International patent application WO2007/088371) was produced by periplasmic expression in a recombinant E. coli strain. The tandab with an overall molecular weight of ca 100 kDa was secreted into the cell periplasm and subsequently into the fermentation growth medium. At the end of fermentation levels of the tandab present in the fermenter supernatant was estimated to be ca. 100 mg/L.

Initial isolation of the tandab involved centrifugation to remove cellular material with subsequent filtration through a 0.45/0.2 micron filter. The resulting clarified solution had a conductivity of ca 31 mS/cm and a pH of 6.9.

Three aliquots of this centrifuged and filtered supernate were dialysed into a matrix of different buffers for 16 hours.

| | Conductivity | |
|---|---|---|
| pH | 5 mS/cm | 15 mS/cm | 30 mS/cm |
| 7 | 25 mM sodium phosphate | 25 mM sodium phosphate, 115 mM NaCl | 25 mM sodium phosphate, 275 mM NaCl |
| 3 | 25 mM sodium citrate | 25 mM sodium citrate, 115 mM NaCl | 25 mM sodium citrate, 275 mM NaCl |

Following dialysis each sample was centrifuged and the solids and supernatant collected separately.

Figure 6:
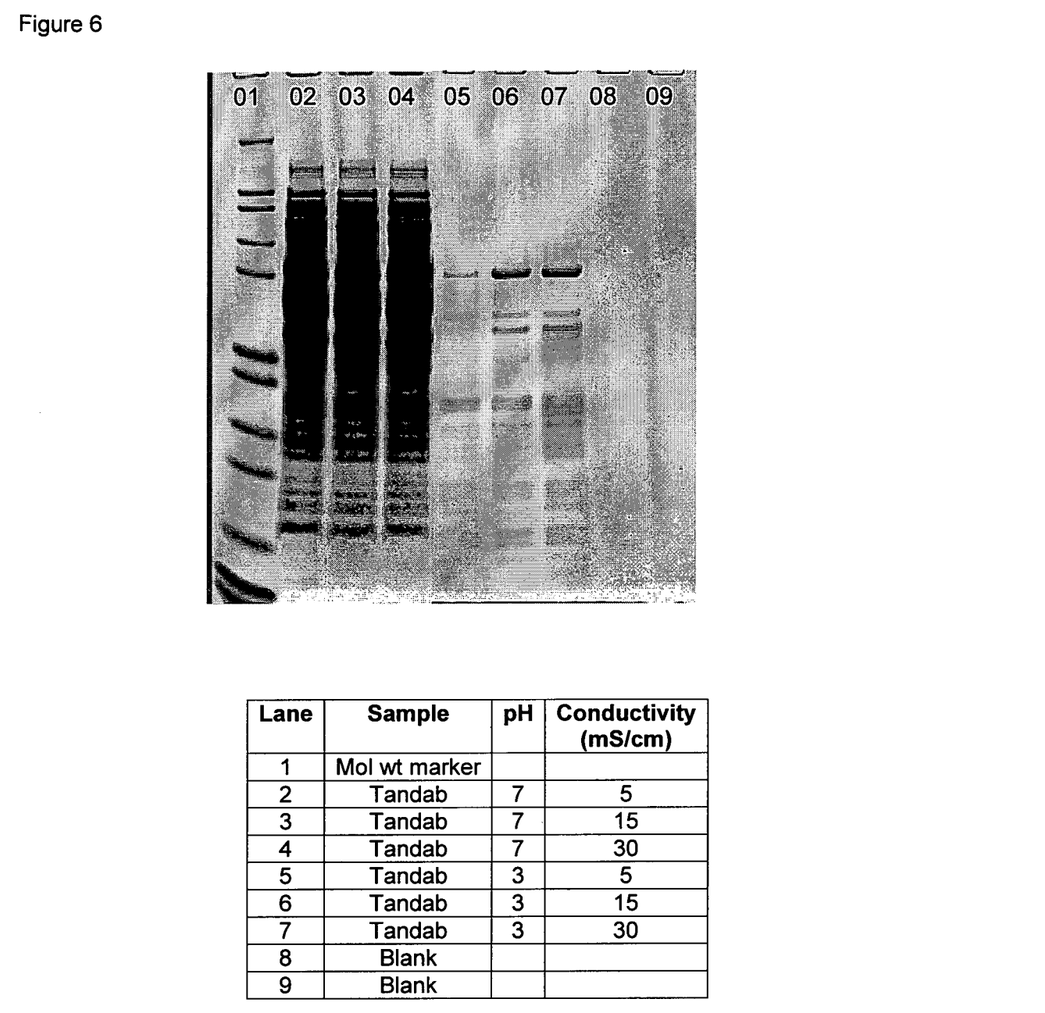
FIG. 6 shows additional SDS PAGE gel results for samples against a sample of the untreated supernate.

Reducing SDS PAGE gels were run of the supernatant fraction for each sample against a sample of the untreated supernate giving the results shown in FIG. 6.

As seen in FIG. 6, the effect of lowering the pH results in a reduction in host cell proteins which is mainly independent of conductivity over the range studied. The tandab antibody fragment was detected in solution by ELISA at similar concentrations at both pH 7 and pH 3 over the range of ionic strengths providing a purification of the antibody fragment relative to the host cell proteins at pH 3.

EXAMPLE 5

An fAb (from the monoclonal anti lysozyme antibody D1.3) was produced by periplasmic expression in a recombinant *E. coli* strain. The fAb with a total molecular weight 47.4 kDa (two chains—a heavy chain comprising a variable light domain with contestant domain attached and a heavy chain comprising a variable light domain with constant domain attached) was secreted into the cell periplasm and subsequently into the fermentation growth medium. At the end of fermentation levels of D1.3 present in the fermenter supernatant were around 100 mg/L.

Initial isolation of fAbD1.3 involved centrifugation to remove cellular material with subsequent filtration through a 0.45/0.2 micron filter. The resulting clarified solution had a conductivity of 29.3 mS/cm and a pH of 6.7.

Three aliquots of this centrifuged and filtered supernate were dialysed into a matrix of different buffers for 16 hours.

| | Conductivity | |
|---|---|---|
| pH | 5 mS/cm | 15 mS/cm | 30 mS/cm |
| 7 | 25 mM sodium phosphate | 25 mM sodium phosphate, 115 mM NaCl | 25 mM sodium phosphate, 275 mM NaCl |
| 5 | 25 mM sodium acetate | 25 mM sodium acetate, 115 mM NaCl | 25 mM sodium acetate, 275 mM NaCl |
| 3 | 25 mM sodium citrate | 25 mM sodium citrate, 115 mM NaCl | 25 mM sodium citrate, 275 mM NaCl |

Following dialysis each sample was centrifuged and the solids and supernatant collected separately.

Figure 7:
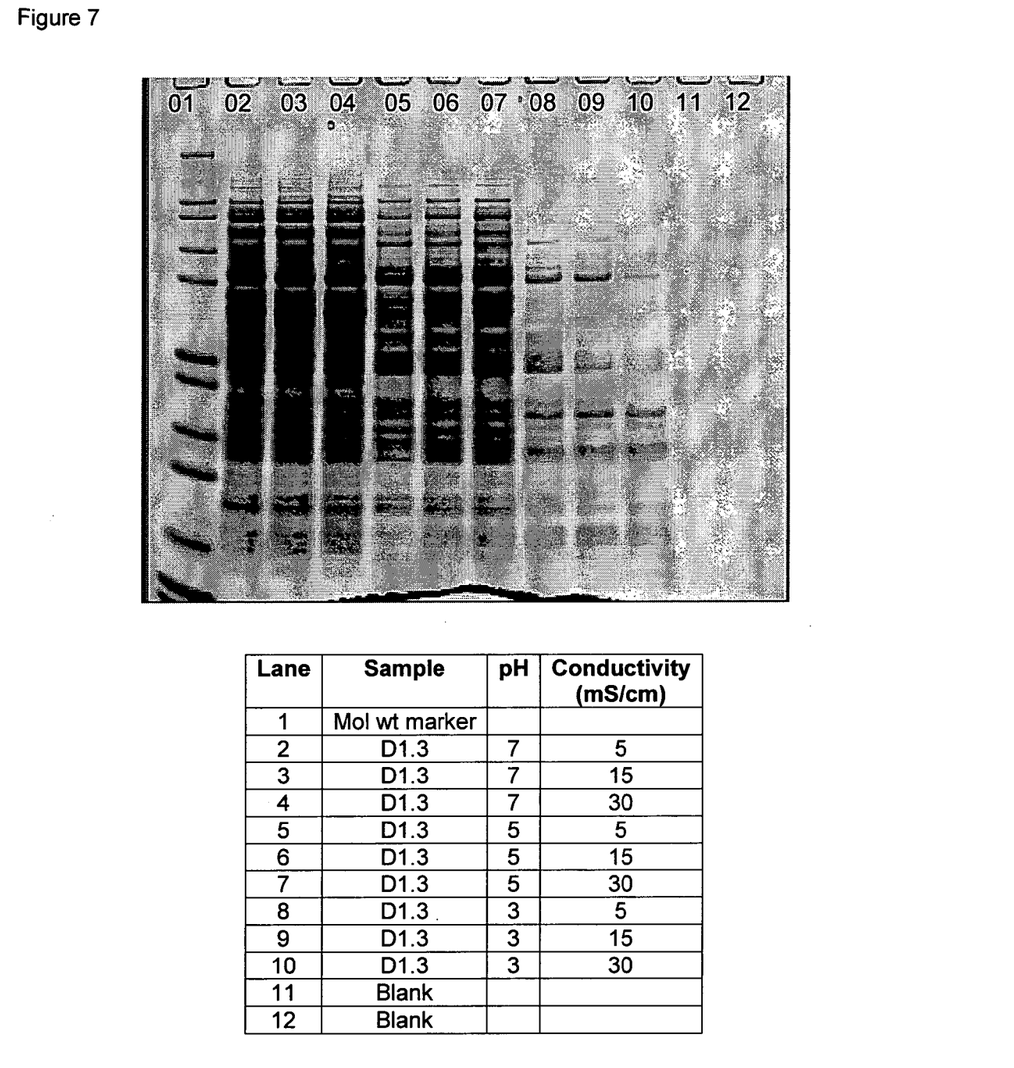
FIG. 7 shows additional SDS PAGE gel results for samples against a sample of the untreated supernate.

Reducing SDS PAGE gels were run of the supernatant fraction for each sample against a sample of the untreated supernate giving the results shown in FIG. 7.

The effect of lowering the pH results in a reduction in host cell proteins which is mainly independent of conductivity over the range studied. The D1.3 antibody fragment was maintained in solution as measured by protein G hplc across the range of pH and ionic strengths providing a purification of the antibody fragment relative to the host cell proteins.

The invention claimed is:

1. A process of purifying a fragment antibody selected from the group consisting of a bispecific ScFv, ScFV fragment, Fab fragment, $Fab_2$, $Fab_3$, minibody, diabody, triabody, single-domain antibody, tetrabody, and multivalent antibody fragment derived tandem antibody fragment from a culture medium comprising at least one impurity comprising:
   separating the fragment antibody from the culture medium, wherein
   the culture medium is prepared by expression of an expression cassette encoding the fragment antibody in a recombinant prokaryotic host cell and subsequent lysis or disruption of the host cell,
   the separation is carried out after reducing the pH of the culture medium to a pH at which the fragment antibody is soluble, but one or more of the impurities are insoluble, and
   if a chromatographic method is performed, said reducing the pH of the culture medium is performed prior to the chromatographic method.

2. A process of purifying a fragment antibody selected from the group consisting of a bispecific ScFv, ScFV fragment, Fab fragment, $Fab_2$, $Fab_3$, minibody, diabody, triabody, single-domain antibody, tetrabody, and multivalent antibody fragment derived tandem antibody fragment comprising:
   a) preparing a culture medium comprising a fragment antibody and at least one impurity by expression of an expression cassette encoding the fragment antibody in a recombinant prokaryotic host cell and subsequent lysis or disruption of the host cell; and
   b) purifying the fragment antibody from the culture medium, wherein the purification is carried out after reducing the pH of the culture medium a pH at which the fragment antibody is soluble, but one or more of the impurities are insoluble,
   wherein if a chromatographic method is performed, said reducing the pH of the culture medium is performed prior to the chromatographic method.

3. A process of separating an impurity from a culture medium comprising a fragment antibody selected from the group consisting of a bispecific ScFv, ScFV fragment, Fab fragment, $Fab_2$, $Fab_3$, minibody, diabody, triabody, single-domain antibody, tetrabody, and multivalent antibody fragment derived tandem antibody fragment and at least one impurity prepared by expression an expression cassette encoding the fragment antibody in a recombinant prokaryotic host cell and subsequent lysis or disruption of the host cell, which comprises
   reducing the pH of the culture medium to a pH at which the fragment antibody is soluble, but one or more of the impurities are insoluble, wherein if a chromatographic method is performed, said reducing the pH of the culture medium is performed prior to the chromatographic method, and
   separating the insoluble impurity from the culture medium.

4. The process according to any one of claims 1 to 3, wherein the pH of the culture medium is from 6 to 8.

5. The process according to claim 4, wherein the pH of the culture medium is from 6.7 to 7.5.

6. The process according to any one of claims 1 to 3, wherein the pH of the culture medium is reduced to a pH less than 6.0.

7. The process according to claim 6, wherein the pH of the culture medium is reduced to a pH in the range of from 3 to 5.

8. The process according to any one of claims 1 to 3, wherein the reduction in pH is accompanied by a reduction in the ionic strength of the culture medium.

9. The process according to claim 8, wherein the ionic strength is reduced to a conductivity of 5 $mScm^{-1}$ or less.

10. The process according to any one of claims 1 to 3, wherein the fragment antibody is subsequently purified by a purification process comprising ion exchange chromatography, hydrophobic interaction chromatography, reverse phase chromatography, hydrophobic charge induction chromatography, mixed mode chromatography, size exclusion chromatography and gel filtration or affinity chromatography.

11. The process according to claim 10, wherein the purification process comprises cation exchange chromatography.

12. The process according to any one of claims 1 to 3, wherein the fragment antibody is an Fab fragment; an ScFv fragment or a single domain antibody.

13. The process according to any one of claims 1 to 3, wherein the host cell is E coli.

14. The process according to claim 13, wherein the E coli is a B or K12 strains thereof.

15. The process according to any one of claims 1 to 3, wherein the pH of the culture medium is from 6 to 8 and is reduced to a pH less than 6, accompanied by a reduction in the ionic strength of the culture medium.

16. The process according to claim 15, wherein the pH of the culture medium is from 6.7 to 7.5 and is reduced to a pH in the range of from 3 to 5, accompanied by a reduction in the ionic strength of the culture medium to a conductivity of 5 $mScm^{-1}$ or less.

17. The process according to claim 16, wherein the fragment antibody is an Fab fragment; an ScFv fragment or a single domain antibody.

18. The process according to claim 1, wherein the reducing the pH is accompanied by a reduction in the ionic strength of the culture medium.

19. A process of producing a purified fragment antibody selected from the group consisting of a bispecific ScFv, ScFV fragment, Fab fragment, $Fab_2$, $Fab_3$, minibody, diabody, triabody, singe-domain antibody, tetrabody, and multivalent antibody fragment derived tandem antibody fragment comprising:

culturing a recombinant prokaryotic host cell containing an expression cassette encoding the fragment antibody under conditions sufficient to produce the fragment antibody, lysing or disrupting the prokaryotic host cell, reducing the pH of the culture medium to a pH at which the fragment antibody is soluble, but one or more impurities are insoluble, and separating the fragment antibody from the culture medium, wherein if a chromatographic method is performed, said reducing and separating are performed prior to the chromatographic method.

20. The process according to claim 19, wherein the reducing comprises dialysing the culture medium against a buffer at a lower pH than the pH of the culture medium.

* * * * *